(12) United States Patent
Hassan et al.

(10) Patent No.: US 7,872,170 B2
(45) Date of Patent: Jan. 18, 2011

(54) GENETIC MARKERS FOR OROBANCHE RESISTANCE IN SUNFLOWER

(75) Inventors: El Sayed Abdel Raouf Sadek Hassan, El Mansoura (EG); Eric Hoeft, Davis, CA (US); Zenglu Li, Ankeny, IA (US); Lomas Tulsieram, Mississauga (CA)

(73) Assignee: Pioneer Hi-Bred International, Inc., Johnston, IA (US)

( * ) Notice: Subject to any disclaimer, the term of this patent is extended or adjusted under 35 U.S.C. 154(b) by 86 days.

(21) Appl. No.: 11/964,784

(22) Filed: Dec. 27, 2007

(65) Prior Publication Data

US 2008/0178325 A1 Jul. 24, 2008

Related U.S. Application Data

(60) Provisional application No. 60/882,279, filed on Dec. 28, 2006.

(51) Int. Cl.
*A01H 1/00* (2006.01)
*A01H 1/02* (2006.01)
*C12N 15/29* (2006.01)
*A01H 5/00* (2006.01)
*C12Q 1/68* (2006.01)

(52) U.S. Cl. .............. 800/265; 800/267; 800/322; 800/301; 800/279; 800/260; 435/6

(58) Field of Classification Search .............. None
See application file for complete search history.

(56) References Cited

FOREIGN PATENT DOCUMENTS

WO 2003073837 A2 9/2003

OTHER PUBLICATIONS

Concibido et al. Crop Science (1997) 37:258-264.*
Westman et al. Theor. Appl. Genet. 96:272-281, 1998.*
Lu et al. Theor Appl Genet (2000) 100:625-632.*
Sunko, S., et al.; "Inheritance of Resistance to Orboa che cer ua Loefl. in Six Sunflower Lines"; Crop Sci (1999) 39:674-678; American Society of Agronomy; Madison, WI US.
Perez-Vich, et al.; "Quantitative trait loci for broomrape (Orobanche cumana Wallr.) resistance in sunflower"; Theor Appl Genet (2004) 109:92-102; Springer Verlag; Berlin/Heidelberg, Germany.
Lai, Z., et al.; "Identification and mapping of SNPs from ESTs in sunflower"; Theor Appl Genet (2005) 111:1532-1544; Springer Verlag; Berlin/Heidelberg, Germany.
Tang, S., et al.; "PCR-multiplexes for a genome-wide framework of simple sequences repeat marker loci in cultivated sunflower"; Theor Appl Genet (2003) 107:6-19; Springer Verlang; Berlin/Heidelberg, Germany.
Yu, J-K., et al.; "Towards a Saturated Molecular Genetic Linkage Map for Cultivated Sunflower"; Crop Sci (2003) 43:367-387; American Society of Agronomy; Madison, WI US.

* cited by examiner

*Primary Examiner*—Medina A Ibrahim

(57) ABSTRACT

Methods for identifying sunflower plants or germplasm that display resistance, improved resistance, or susceptibility to *Orobanche cumana* are provided. Sunflower plants or germplasm that are resistant or have improved resistance to *Orobanche cumana* are created. The plants or germplasm produced by the methods of the invention are also an aspect of the invention.

11 Claims, 8 Drawing Sheets

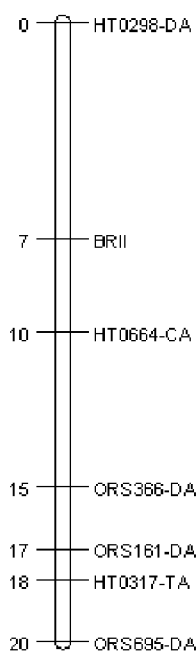
Figure 1. Location of a broomrape system 2 resistance gene ("BRII" or "BRSII") positioned to LG-04 in an F2:3 mapping population from the cross of U0151LG x E0005LG.

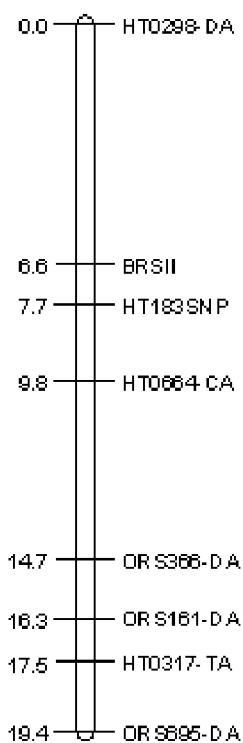
Figure 2. Location of SNP marker HT183 with reference to broomrape system 2 resistance gene.

FIG. 3A

```
BestFit Results
BestFit Results

BESTFIT of: BRSII-resistant_allele  check: 5999  from: 1  to: 278

WPDEF from CMI to: BRSII-susc_allele  check: 5510  from: 1  to: 278

WPDEF from CMI

Symbol comparison table: swgapdna.cmp CompCheck: 2335

Gap Weight:     50      Average Match: 10.000
      Length Weight:      3   Average Mismatch: -9.000

Quality:   2723            Length:    278
              Ratio:  9.795              Gaps:      0
 Percent Similarity: 98.921   Percent Identity: 98.921

Match display thresholds for the alignment(s):
                    | = IDENTITY
                    : =   5
                    . =   1

BRSII-resistant_allele x BRSII-susc_allele December 27, 2006 17:08  ..

.         .         .         .         .
    1 ATCAACCCGCAGTGAACCCGCAAGGGGTCAGATTCACGGGTTCCGTATGG 50
      ||||||||||||||||||||||||||||||||||||||||||||||||||
    1 ATCAACCCGCAGTGAACCCGCAAGGGGTCAGATTCACGGGTTCCGTATGG 50

.         .         .         .         .
   51 CTTTATGGTATGAACACTTAGGCATGCTCGACGACACTTTCCAGAACCCA 100
      ||||||||||||||||||||||||||||||||||||||||||||||||||
   51 CTTTATGGTATGAACACTTAGGCATGCTCGACGACACTTTCCAGAACCCA 100

**   .         .         .         .  *      .
  101 GAAAATACCGAGTGTGTGAAAAAAGTTAACCACATGGCCGAAAAATATTG 150
      ||||  |||||||||||||||||||||||||||||||||||| |||||||
  101 GAAAGCACCGAGTGTGTGAAAAAAGTTAACCACATGGCCGACAAATATTG 150

.         .         .         .         .
  151 GGACCTTTTCGCTAGTGAGAATCTTGAACAAGACCTGCCCGGTCACTTGC 200
      ||||||||||||||||||||||||||||||||||||||||||||||||||
  151 GGACCTTTTCGCTAGTGAGAATCTTGAACAAGACCTGCCCGGTCACTTGC 200

.         .         .         .         .
  201 TTCGTTACCCGATCGGGGTTGCTAGTGAAGGTAATGTGACCGAACTGCCC 250
      ||||||||||||||||||||||||||||||||||||||||||||||||||
  201 TTCGTTACCCGATCGGGGTTGCTAGTGAAGGTAATGTGACCGAACTGCCC 250

.         .
  251 GGAACCGAGTTTTTCCCTGATACGAAAG 278
      ||||||||||||||||||||||||||||
  251 GGAACCGAGTTTTTCCCTGATACGAAAG 278
```

FIG. 3B

```
Input Sequence: BRSII-resistant_allele

!!NA_SEQUENCE 1.0
WPDEF from CMI
BRSII-resistant_allele  Length: 278  August 28, 2006 18:19  Type: N
Check: 5999  ..

1  ATCAACCCGC AGTGAACCCG CAAGGGGTCA GATTCACGGG TTCCGTATGG

51  CTTTATGGTA TGAACACTTA GGCATGCTCG ACGACACTTT CCAGAACCCA

101  GAAAATACCG AGTGTGTGAA AAAAGTTAAC CACATGGCCG AAAAATATTG

151  GGACCTTTTC GCTAGTGAGA ATCTTGAACA AGACCTGCCC GGTCACTTGC

201  TTCGTTACCC GATCGGGGTT GCTAGTGAAG GTAATGTGAC CGAACTGCCC

251  GGAACCGAGT TTTTCCCTGA TACGAAAG
```

```
Input Sequence: BRSII-susc_allele

!!NA_SEQUENCE 1.0
WPDEF from CMI
BRSII-susc_allele  Length: 278  August 28, 2006 18:18  Type: N  Check:
5510  ..

1  ATCAACCCGC AGTGAACCCG CAAGGGGTCA GATTCACGGG TTCCGTATGG

51  CTTTATGGTA TGAACACTTA GGCATGCTCG ACGACACTTT CCAGAACCCA

101  GAAAGCACCG AGTGTGTGAA AAAAGTTAAC CACATGGCCG ACAAATATTG

151  GGACCTTTTC GCTAGTGAGA ATCTTGAACA AGACCTGCCC GGTCACTTGC

201  TTCGTTACCC GATCGGGGTT GCTAGTGAAG GTAATGTGAC CGAACTGCCC

251  GGAACCGAGT TTTTCCCTGA TACGAAAG
```

FIG. 4A

Additional F2 Population for Marker Development Of System 2 Resistance:

| | | | Parents | |
|---|---|---|---|---|
| Source | Pedigree | Broomrape reaction | Susceptible parent | Resistant parent |
| 04UA4025-1 | E0012LG/U0151LG)GUX1 | Resistant | E0012LG | U0151LG |
| 04UA4025-2 | E0012LG/U0151LG)GUX2 | Resistant | E0012LG | U0151LG |
| 04UA4025-3 | E0012LG/U0151LG)GUX3 | Resistant | E0012LG | U0151LG |
| 04UA4025-4 | E0012LG/U0151LG)GUX4 | Resistant | E0012LG | U0151LG |
| 04UA4025-5 | E0012LG/U0151LG)GUX5 | Resistant | E0012LG | U0151LG |
| 04UA4025-6 | E0012LG/U0151LG)GUX6 | Resistant | E0012LG | U0151LG |
| 04UA4025-7 | E0012LG/U0151LG)GUX7 | Resistant | E0012LG | U0151LG |
| 04UA4025-8 | E0012LG/U0151LG)GUX8 | Resistant | E0012LG | U0151LG |
| 04UA4025-9 | E0012LG/U0151LG)GUX9 | Resistant | E0012LG | U0151LG |
| 04UA4025-A0 | E0012LG/U0151LG)GUXA0 | Resistant | E0012LG | U0151LG |
| 04UA4025-A1 | E0012LG/U0151LG)GUXA1 | Resistant | E0012LG | U0151LG |
| 04UA4025-C1 | E0012LG/U0151LG)GUXC1 | Susceptible | E0012LG | U0151LG |
| 04UA4025-C2 | E0012LG/U0151LG)GUXC2 | Susceptible | E0012LG | U0151LG |
| 04UA4025-C3 | E0012LG/U0151LG)GUXC3 | Susceptible | E0012LG | U0151LG |
| 04UA4025-C4 | E0012LG/U0151LG)GUXC4 | Susceptible | E0012LG | U0151LG |
| 04UA4025-C5 | E0012LG/U0151LG)GUXC5 | Susceptible | E0012LG | U0151LG |
| 04UA4025-C6 | E0012LG/U0151LG)GUXC6 | Susceptible | E0012LG | U0151LG |
| 04UA4025-C7 | E0012LG/U0151LG)GUXC7 | Susceptible | E0012LG | U0151LG |
| 04UA4025-C8 | E0012LG/U0151LG)GUXC8 | Susceptible | E0012LG | U0151LG |
| 04UA4025-C9 | E0012LG/U0151LG)GUXC9 | Susceptible | E0012LG | U0151LG |
| 04UA4025-D0 | E0012LG/U0151LG)GUXD0 | Susceptible | E0012LG | U0151LG |
| 04UA4025-D1 | E0012LG/U0151LG)GUXD1 | Susceptible | E0012LG | U0151LG |
| | | | | |
| 04UA4026-1 | N0241LG/U0151LG)GUX1 | Resistant | N0241LG | U0151LG |
| 04UA4026-2 | N0241LG/U0151LG)GUX2 | Resistant | N0241LG | U0151LG |
| 04UA4026-3 | N0241LG/U0151LG)GUX3 | Resistant | N0241LG | U0151LG |
| 04UA4026-4 | N0241LG/U0151LG)GUX4 | Resistant | N0241LG | U0151LG |
| 04UA4026-5 | N0241LG/U0151LG)GUX5 | Resistant | N0241LG | U0151LG |
| 04UA4026-6 | N0241LG/U0151LG)GUX6 | Resistant | N0241LG | U0151LG |
| 04UA4026-7 | N0241LG/U0151LG)GUX7 | Resistant | N0241LG | U0151LG |
| 04UA4026-8 | N0241LG/U0151LG)GUX8 | Resistant | N0241LG | U0151LG |
| 04UA4026-9 | N0241LG/U0151LG)GUX9 | Resistant | N0241LG | U0151LG |
| 04UA4026-A0 | N0241LG/U0151LG)GUXA0 | Resistant | N0241LG | U0151LG |
| 04UA4026-A1 | N0241LG/U0151LG)GUXA1 | Resistant | N0241LG | U0151LG |
| 04UA4026-A2 | N0241LG/U0151LG)GUXA2 | Resistant | N0241LG | U0151LG |
| 04UA4026-A3 | N0241LG/U0151LG)GUXA3 | Resistant | N0241LG | U0151LG |
| 04UA4026-A4 | N0241LG/U0151LG)GUXA4 | Resistant | N0241LG | U0151LG |
| 04UA4026-A5 | N0241LG/U0151LG)GUXA5 | Resistant | N0241LG | U0151LG |
| 04UA4026-A6 | N0241LG/U0151LG)GUXA6 | Resistant | N0241LG | U0151LG |
| 04UA4026-A7 | N0241LG/U0151LG)GUXA7 | Resistant | N0241LG | U0151LG |
| 04UA4026-A8 | N0241LG/U0151LG)GUXA8 | Resistant | N0241LG | U0151LG |
| 04UA4026-A9 | N0241LG/U0151LG)GUXA9 | Resistant | N0241LG | U0151LG |
| 04UA4026-B0 | N0241LG/U0151LG)GUXB0 | Resistant | N0241LG | U0151LG |
| 04UA4026-C1 | N0241LG/U0151LG)GUXC1 | Susceptible | N0241LG | U0151LG |
| 04UA4026-C2 | N0241LG/U0151LG)GUXC2 | Susceptible | N0241LG | U0151LG |

| | | | | |
|---|---|---|---|---|
| 04UA4026-C3 | N0241LG/U0151LG)GUXC3 | Susceptible | N0241LG | U0151LG |

FIG. 4B

| | | | | |
|---|---|---|---|---|
| 04UA4026-C4 | N0241LG/U0151LG)GUXC4 | Susceptible | N0241LG | U0151LG |
| 04UA4026-C5 | N0241LG/U0151LG)GUXC5 | Susceptible | N0241LG | U0151LG |
| 04UA4026-C6 | N0241LG/U0151LG)GUXC6 | Susceptible | N0241LG | U0151LG |
| 04UA4026-C7 | N0241LG/U0151LG)GUXC7 | Susceptible | N0241LG | U0151LG |
| 04UA4026-C8 | N0241LG/U0151LG)GUXC8 | Susceptible | N0241LG | U0151LG |
| 04UA4026-C9 | N0241LG/U0151LG)GUXC9 | Susceptible | N0241LG | U0151LG |
| 04UA4026-D0 | N0241LG/U0151LG)GUXD0 | Susceptible | N0241LG | U0151LG |
| 04UA4026-D1 | N0241LG/U0151LG)GUXD1 | Susceptible | N0241LG | U0151LG |
| 04UA4026-D2 | N0241LG/U0151LG)GUXD2 | Susceptible | N0241LG | U0151LG |
| 04UA4026-D3 | N0241LG/U0151LG)GUXD3 | Susceptible | N0241LG | U0151LG |
| 04UA4026-D4 | N0241LG/U0151LG)GUXD4 | Susceptible | N0241LG | U0151LG |
| | | | | |
| 04UA4028-1 | N0244LG/U0151LG)GUX1 | Resistant | N0244LG | U0151LG |
| 04UA4028-2 | N0244LG/U0151LG)GUX2 | Resistant | N0244LG | U0151LG |
| 04UA4028-3 | N0244LG/U0151LG)GUX3 | Resistant | N0244LG | U0151LG |
| 04UA4028-4 | N0244LG/U0151LG)GUX4 | Resistant | N0244LG | U0151LG |
| 04UA4028-5 | N0244LG/U0151LG)GUX5 | Resistant | N0244LG | U0151LG |
| 04UA4028-6 | N0244LG/U0151LG)GUX6 | Resistant | N0244LG | U0151LG |
| 04UA4028-7 | N0244LG/U0151LG)GUX7 | Resistant | N0244LG | U0151LG |
| 04UA4028-8 | N0244LG/U0151LG)GUX8 | Resistant | N0244LG | U0151LG |
| 04UA4028-9 | N0244LG/U0151LG)GUX9 | Resistant | N0244LG | U0151LG |
| 04UA4028-A0 | N0244LG/U0151LG)GUXA0 | Resistant | N0244LG | U0151LG |
| 04UA4028-A1 | N0244LG/U0151LG)GUXA1 | Resistant | N0244LG | U0151LG |
| 04UA4028-A2 | N0244LG/U0151LG)GUXA2 | Resistant | N0244LG | U0151LG |
| 04UA4028-A3 | N0244LG/U0151LG)GUXA3 | Resistant | N0244LG | U0151LG |
| 04UA4028-A4 | N0244LG/U0151LG)GUXA4 | Resistant | N0244LG | U0151LG |
| 04UA4028-A5 | N0244LG/U0151LG)GUXA5 | Resistant | N0244LG | U0151LG |
| 04UA4028-A6 | N0244LG/U0151LG)GUXA6 | Resistant | N0244LG | U0151LG |
| 04UA4028-A7 | N0244LG/U0151LG)GUXA7 | Resistant | N0244LG | U0151LG |
| 04UA4028-A8 | N0244LG/U0151LG)GUXA8 | Resistant | N0244LG | U0151LG |
| 04UA4028-C1 | N0244LG/U0151LG)GUXC1 | Susceptible | N0244LG | U0151LG |
| 04UA4028-C2 | N0244LG/U0151LG)GUXC2 | Susceptible | N0244LG | U0151LG |
| 04UA4028-C3 | N0244LG/U0151LG)GUXC3 | Susceptible | N0244LG | U0151LG |
| 04UA4028-C4 | N0244LG/U0151LG)GUXC4 | Susceptible | N0244LG | U0151LG |
| 04UA4028-C5 | N0244LG/U0151LG)GUXC5 | Susceptible | N0244LG | U0151LG |
| 04UA4028-C6 | N0244LG/U0151LG)GUXC6 | Susceptible | N0244LG | U0151LG |
| 04UA4028-C7 | N0244LG/U0151LG)GUXC7 | Susceptible | N0244LG | U0151LG |
| 04UA4028-C8 | N0244LG/U0151LG)GUXC8 | Susceptible | N0244LG | U0151LG |
| 04UA4028-C9 | N0244LG/U0151LG)GUXC9 | Susceptible | N0244LG | U0151LG |
| 04UA4028-D0 | N0244LG/U0151LG)GUXD0 | Susceptible | N0244LG | U0151LG |
| 04UA4028-D1 | N0244LG/U0151LG)GUXD1 | Susceptible | N0244LG | U0151LG |
| 04UA4028-D2 | N0244LG/U0151LG)GUXD2 | Susceptible | N0244LG | U0151LG |
| 04UA4028-D3 | N0244LG/U0151LG)GUXD3 | Susceptible | N0244LG | U0151LG |
| 04UA4028-D4 | N0244LG/U0151LG)GUXD4 | Susceptible | N0244LG | U0151LG |
| 04UA4028-D5 | N0244LG/U0151LG)GUXD5 | Susceptible | N0244LG | U0151LG |
| 04UA4028-D6 | N0244LG/U0151LG)GUXD6 | Susceptible | N0244LG | U0151LG |

FIG. 4C

| 04UA4043-1 | =IF2603G/U0151LG)GUX1 | Resistant | INR2603B | U0151LG |
|---|---|---|---|---|
| 04UA4043-2 | =IF2603G/U0151LG)GUX2 | Resistant | INR2603B | U0151LG |
| 04UA4043-3 | =IF2603G/U0151LG)GUX3 | Resistant | INR2603B | U0151LG |
| 04UA4043-4 | =IF2603G/U0151LG)GUX4 | Resistant | INR2603B | U0151LG |
| 04UA4043-5 | =IF2603G/U0151LG)GUX5 | Resistant | INR2603B | U0151LG |
| 04UA4043-6 | =IF2603G/U0151LG)GUX6 | Resistant | INR2603B | U0151LG |
| 04UA4043-7 | =IF2603G/U0151LG)GUX7 | Resistant | INR2603B | U0151LG |
| 04UA4043-8 | =IF2603G/U0151LG)GUX8 | Resistant | INR2603B | U0151LG |
| 04UA4043-9 | =IF2603G/U0151LG)GUX9 | Resistant | INR2603B | U0151LG |
| 04UA4043-A0 | =IF2603G/U0151LG)GUXA0 | Resistant | INR2603B | U0151LG |
| 04UA4043-A1 | =IF2603G/U0151LG)GUXA1 | Resistant | INR2603B | U0151LG |
| 04UA4043-A2 | =IF2603G/U0151LG)GUXA2 | Resistant | INR2603B | U0151LG |
| 04UA4043-A3 | =IF2603G/U0151LG)GUXA3 | Resistant | INR2603B | U0151LG |
| 04UA4043-A4 | =IF2603G/U0151LG)GUXA4 | Resistant | INR2603B | U0151LG |
| 04UA4043-A5 | =IF2603G/U0151LG)GUXA5 | Resistant | INR2603B | U0151LG |
| 04UA4043-A6 | =IF2603G/U0151LG)GUXA6 | Resistant | INR2603B | U0151LG |
| 04UA4043-A7 | =IF2603G/U0151LG)GUXA7 | Resistant | INR2603B | U0151LG |
| 04UA4043-A8 | =IF2603G/U0151LG)GUXA8 | Resistant | INR2603B | U0151LG |
| 04UA4043-A9 | =IF2603G/U0151LG)GUXA9 | Resistant | INR2603B | U0151LG |
| 04UA4043-B0 | =IF2603G/U0151LG)GUXB0 | Resistant | INR2603B | U0151LG |
| 04UA4043-B1 | =IF2603G/U0151LG)GUXB1 | Resistant | INR2603B | U0151LG |
| 04UA4043-B2 | =IF2603G/U0151LG)GUXB2 | Resistant | INR2603B | U0151LG |
| 04UA4043-B3 | =IF2603G/U0151LG)GUXB3 | Resistant | INR2603B | U0151LG |
| 04UA4043-B4 | =IF2603G/U0151LG)GUXB4 | Resistant | INR2603B | U0151LG |
| 04UA4043-B5 | =IF2603G/U0151LG)GUXB5 | Resistant | INR2603B | U0151LG |
| 04UA4043-B6 | =IF2603G/U0151LG)GUXB6 | Resistant | INR2603B | U0151LG |
| 04UA4043-B7 | =IF2603G/U0151LG)GUXB7 | Resistant | INR2603B | U0151LG |
| 04UA4043-B8 | =IF2603G/U0151LG)GUXB8 | Resistant | INR2603B | U0151LG |
| 04UA4043-B9 | =IF2603G/U0151LG)GUXB9 | Resistant | INR2603B | U0151LG |
| 04UA4043-C0 | =IF2603G/U0151LG)GUXC0 | Resistant | INR2603B | U0151LG |
| 04UA4043-C1 | =IF2603G/U0151LG)GUXC1 | Susceptible | INR2603B | U0151LG |
| 04UA4043-C2 | =IF2603G/U0151LG)GUXC2 | Susceptible | INR2603B | U0151LG |
| 04UA4043-C3 | =IF2603G/U0151LG)GUXC3 | Susceptible | INR2603B | U0151LG |
| 04UA4043-C4 | =IF2603G/U0151LG)GUXC4 | Susceptible | INR2603B | U0151LG |
| 04UA4043-C5 | =IF2603G/U0151LG)GUXC5 | Susceptible | INR2603B | U0151LG |
| 04UA4043-C6 | =IF2603G/U0151LG)GUXC6 | Susceptible | INR2603B | U0151LG |
| 04UA4043-C7 | =IF2603G/U0151LG)GUXC7 | Susceptible | INR2603B | U0151LG |
| 04UA4043-C8 | =IF2603G/U0151LG)GUXC8 | Susceptible | INR2603B | U0151LG |
| 04UA4043-C9 | =IF2603G/U0151LG)GUXC9 | Susceptible | INR2603B | U0151LG |
| 04UA4043-D0 | =IF2603G/U0151LG)GUXD0 | Susceptible | INR2603B | U0151LG |
| | | | | |
| 04UA4042-1 | =IF2603G/U0278LG)GUX1 | Resistant | INR2603B | U0278LG |
| 04UA4042-2 | =IF2603G/U0278LG)GUX2 | Resistant | INR2603B | U0278LG |
| 04UA4042-3 | =IF2603G/U0278LG)GUX3 | Resistant | INR2603B | U0278LG |
| 04UA4042-4 | =IF2603G/U0278LG)GUX4 | Resistant | INR2603B | U0278LG |
| 04UA4042-5 | =IF2603G/U0278LG)GUX5 | Resistant | INR2603B | U0278LG |
| 04UA4042-6 | =IF2603G/U0278LG)GUX6 | Resistant | INR2603B | U0278LG |
| 04UA4042-7 | =IF2603G/U0278LG)GUX7 | Resistant | INR2603B | U0278LG |
| 04UA4042-8 | =IF2603G/U0278LG)GUX8 | Resistant | INR2603B | U0278LG |

FIG. 4D

| 04UA4042-9 | =IF2603G/U0278LG)GUX9 | Resistant | INR2603B | U0278LG |
|---|---|---|---|---|
| 04UA4042-A0 | =IF2603G/U0278LG)GUXA0 | Resistant | INR2603B | U0278LG |
| 04UA4042-A1 | =IF2603G/U0278LG)GUXA1 | Resistant | INR2603B | U0278LG |
| 04UA4042-A2 | =IF2603G/U0278LG)GUXA2 | Resistant | INR2603B | U0278LG |
| 04UA4042-A3 | =IF2603G/U0278LG)GUXA3 | Resistant | INR2603B | U0278LG |
| 04UA4042-A4 | =IF2603G/U0278LG)GUXA4 | Resistant | INR2603B | U0278LG |
| 04UA4042-A5 | =IF2603G/U0278LG)GUXA5 | Resistant | INR2603B | U0278LG |
| 04UA4042-A6 | =IF2603G/U0278LG)GUXA6 | Resistant | INR2603B | U0278LG |
| 04UA4042-A7 | =IF2603G/U0278LG)GUXA7 | Resistant | INR2603B | U0278LG |
| 04UA4042-A8 | =IF2603G/U0278LG)GUXA8 | Resistant | INR2603B | U0278LG |
| 04UA4042-A9 | =IF2603G/U0278LG)GUXA9 | Resistant | INR2603B | U0278LG |
| 04UA4042-C1 | =IF2603G/U0278LG)GUXC1 | Susceptible | INR2603B | U0278LG |
| 04UA4042-C2 | =IF2603G/U0278LG)GUXC2 | Susceptible | INR2603B | U0278LG |
| 04UA4042-C3 | =IF2603G/U0278LG)GUXC3 | Susceptible | INR2603B | U0278LG |
| 04UA4042-C4 | =IF2603G/U0278LG)GUXC4 | Susceptible | INR2603B | U0278LG |
| 04UA4042-C5 | =IF2603G/U0278LG)GUXC5 | Susceptible | INR2603B | U0278LG |
| 04UA4042-C6 | =IF2603G/U0278LG)GUXC6 | Susceptible | INR2603B | U0278LG |
| 04UA4042-C7 | =IF2603G/U0278LG)GUXC7 | Susceptible | INR2603B | U0278LG |
| 04UA4042-C8 | =IF2603G/U0278LG)GUXC8 | Susceptible | INR2603B | U0278LG |
| 04UA4042-C9 | =IF2603G/U0278LG)GUXC9 | Susceptible | INR2603B | U0278LG |
| 04UA4042-D0 | =IF2603G/U0278LG)GUXD0 | Susceptible | INR2603B | U0278LG |
| 04UA4042-D1 | =IF2603G/U0278LG)GUXD1 | Susceptible | INR2603B | U0278LG |
| 04UA4042-D2 | =IF2603G/U0278LG)GUXD2 | Susceptible | INR2603B | U0278LG |
| 04UA4042-D3 | =IF2603G/U0278LG)GUXD3 | Susceptible | INR2603B | U0278LG |
| 04UA4042-D4 | =IF2603G/U0278LG)GUXD4 | Susceptible | INR2603B | U0278LG |
| 04UA4042-D5 | =IF2603G/U0278LG)GUXD5 | Susceptible | INR2603B | U0278LG |
| 04UA4042-D6 | =IF2603G/U0278LG)GUXD6 | Susceptible | INR2603B | U0278LG |
| 04UA4042-D7 | =IF2603G/U0278LG)GUXD7 | Susceptible | INR2603B | U0278LG |
| 04UA4042-D8 | =IF2603G/U0278LG)GUXD8 | Susceptible | INR2603B | U0278LG |

169

Parents

| 03UA4897-1 | N0241LG | Susceptible | | |
|---|---|---|---|---|
| 03UA4902-1 | N0244LG | Susceptible | | |
| 03UA5038-2 | INR2603B | Susceptible | | |
| 04UA4964-1 | U0278LG | Resistant | | |
| 04UA4975-1 | U0151LG | Resistant | | |
| 04UA5586-1 | E0012LG | Susceptible | | |

| Source | Pedigree | Susceptible parent | Resistant parent |
|---|---|---|---|
| 04UA4025 | E0012LG/U0151LG)GUX1 | E0012LG | U0151LG |
| 04UA4026 | N0241LG/U0151LG)GUX1 | N0241LG | U0151LG |
| 04UA4028 | N0244LG/U0151LG)GUX1 | N0244LG | U0151LG |
| 04UA4043 | =IF2603G/U0151LG)GUX1 | INR2603B | U0151LG |
| 04UA4042 | =IF2603G/U0278LG)GUX1 | INR2603B | U0278LG |

SEQUENCE LISTING

<160> NUMBER OF SEQ ID NOS: 10

<210> SEQ ID NO 1
<211> LENGTH: 278
<212> TYPE: DNA
<213> ORGANISM: Helianthus annuus

<400> SEQUENCE: 1

-continued

```
atcaacccgc agtgaacccg caaggggtca gattcacggg ttccgtatgg ctttatggta     60
tgaacactta ggcatgctcg acgacacttt ccagaaccca gaaagcaccg agtgtgtgaa    120
aaaagttaac cacatggccg acaaatattg ggaccttttc gctagtgaga atcttgaaca    180
agacctgccc ggtcacttgc ttcgttaccc gatcggggtt gctagtgaag gtaatgtgac    240
cgaactgccc ggaaccgagt ttttccctga tacgaaag                            278
```

<210> SEQ ID NO 2
<211> LENGTH: 278
<212> TYPE: DNA
<213> ORGANISM: Helianthus annuus

<400> SEQUENCE: 2

```
atcaacccgc agtgaacccg caaggggtca gattcacggg ttccgtatgg ctttatggta     60
tgaacactta ggcatgctcg acgacacttt ccagaaccca gaaaataccg agtgtgtgaa    120
aaaagttaac cacatggccg aaaaatattg ggaccttttc gctagtgaga atcttgaaca    180
agacctgccc ggtcacttgc ttcgttaccc gatcggggtt gctagtgaag gtaatgtgac    240
cgaactgccc ggaaccgagt ttttccctga tacgaaag                            278
```

<210> SEQ ID NO 3
<211> LENGTH: 16
<212> TYPE: DNA
<213> ORGANISM: Artificial Sequence
<220> FEATURE:
<223> OTHER INFORMATION: BRSII-Marker #1 - Probe-1

<400> SEQUENCE: 3

```
acccagaaag caccga                                                     16
```

<210> SEQ ID NO 4
<211> LENGTH: 17
<212> TYPE: DNA
<213> ORGANISM: Artificial Sequence
<220> FEATURE:
<223> OTHER INFORMATION: BRSII-Marker #1 - Probe-2

<400> SEQUENCE: 4

```
acccagaaaa taccgag                                                    17
```

<210> SEQ ID NO 5
<211> LENGTH: 21
<212> TYPE: DNA
<213> ORGANISM: Artificial Sequence
<220> FEATURE:
<223> OTHER INFORMATION: BRSII-Marker #1 - forward primer

<400> SEQUENCE: 5

```
taggcatgct cgacgacact t                                               21
```

<210> SEQ ID NO 6
<211> LENGTH: 23
<212> TYPE: DNA
<213> ORGANISM: Artificial Sequence
<220> FEATURE:
<223> OTHER INFORMATION: BRSII-Marker #1 - reverse primer

<400> SEQUENCE: 6

```
tatttgtcgg ccatgtggtt aac                                             23
```

<210> SEQ ID NO 7
<211> LENGTH: 17

-continued

```
<212> TYPE: DNA
<213> ORGANISM: Artificial Sequence
<220> FEATURE:
<223> OTHER INFORMATION: BRSII Marker #2 Probe-Susceptible

<400> SEQUENCE: 7
tcccaatatt tgtcggc                                                  17

<210> SEQ ID NO 8
<211> LENGTH: 19
<212> TYPE: DNA
<213> ORGANISM: Artificial Sequence
<220> FEATURE:
<223> OTHER INFORMATION: BRSII Marker #2  Probe-Resistant

<400> SEQUENCE: 8
tcccaatatt tttcggcca                                                19

<210> SEQ ID NO 9
<211> LENGTH: 25
<212> TYPE: DNA
<213> ORGANISM: Artificial Sequence
<220> FEATURE:
<223> OTHER INFORMATION: BRSII Marker #2 Reverse primer

<400> SEQUENCE: 9
accgagtgtg tgaaaaaagt taacc                                         25

<210> SEQ ID NO 10
<211> LENGTH: 25
<212> TYPE: DNA
<213> ORGANISM: Artificial Sequence
<220> FEATURE:
<223> OTHER INFORMATION: BRSII Marker #2 Forward primer

<400> SEQUENCE: 10
tgttcaagat tctcactagc gaaaa                                         25
```

GENETIC MARKERS FOR OROBANCHE RESISTANCE IN SUNFLOWER

CROSS-REFERENCE TO RELATED APPLICATIONS

This application claims priority to, and hereby incorporates by reference, U.S. Provisional Patent Application 60/882,279 filed on Dec. 28, 2006.

FIELD OF THE INVENTION

This invention relates to compositions and methods for using molecular genetic markers to characterize sunflower germplasm for resistance to *Orobanche cumana*.

BACKGROUND

Cultivated sunflower (*Helianthus annuus* L.) is being grown as an increasingly important oilseed crop in many temperate, semi-dry regions of the world.

The cultivated sunflower is a major worldwide source of vegetable oil. Oil types of sunflowers contain 40 to 48 percent or more oil in the seed. Sunflower oil is valued as an edible oil because of its high unsaturated fat level and light color. Sunflower oil is used for salads, cooking oil or margarine. The protein content of sunflower meal prepared from seeds after oil extraction is useful as livestock feed. The seeds from both oil and confectionery varieties of cultivated sunflower are useful as bird food.

The parasitic plant broomrape (*Orobanche* Spp.) has become a limiting factor for sunflower crops in infested countries. The decrease in crop yield can reach 95% in an affected field. Particular *Orobanche* species afflicting sunflower include *Orobanche aegyptiaca* Pers., *O. ramosa* L., *O. minor* Sm., *O. cumana* Wallr. and *O. cernua* Loefl.

*Orobanche cumana* Wallr. (also known as *O. cernua* Loefl.) is a severe pest in sunflower in eastern Europe and has been spreading through southern Europe. Over the past few years the progression of this parasitic plant, its introduction into new countries and the development of new and more virulent races have all been observed. *Orobanche* presents a worldwide risk, and some species such as *O. minor* have appeared as exotics in the United States.

Starting in 1996, the emergence of three new races of broomrape was observed in fields in Turkey, Spain and Bulgaria. By 2000, the number of affected fields in these areas had sharply increased. Some producers had stopped growing sunflower because of the significant reduction in grain yield experienced.

These weeds are obligate root holoparasites. *Orobanche* species are very difficult to eliminate because except for their flower parts, they live in the soil; their seeds are minute and prolifically produced, easily dispersed and very long-lived. Thus, herbicides presently used in sunflower generally provide inadequate control.

Means of controlling *Orobanche* include biological control agents, isolation of the genes responsible for *Orobanche* resistance in sunflower, and development of resistant sunflower lines.

It has been reported that *Fusarium oxysporum* f. sp. *orthoceras* may be a potential agent for the biological control of *Orobanche cumana* (Thomas-Heiko, et al., (September 1998) *Biological Control*. 13(1):41-48). However, application methods and uniform doses under field conditions have yet to be determined.

The Or3 gene confers resistance to *Orobanche* attack but is known to be efficacious only against race C. At least six race variants of *Orobanche* have been reported (Pérez-Vich, et al., (2004) *Theor. Appl. Gen.* 109:92-102; Antonova, T. S., et al., (1996) *Weed Research* 36(2):113-121).

Identification and utilization of additional sources of resistance to *Orobanche* is beneficial in managing race shifts and minimizing production loss.

BRIEF DESCRIPTION OF THE INVENTION

This invention relates to compositions and methods of use of genetic markers for characterization of sunflower germplasm with respect to System 2 resistance to *Orobanche cumana*. Plants and lines identified as having highly heritable *Orobanche* resistance traits are useful in developing commercial cultivars of sunflower crops having valuable agronomic and/or seed quality traits.

BRIEF DESCRIPTION OF THE DRAWINGS

FIG. 1 provides a partial marker map of sunflower linkage group 4, including the position of a putative broomrape System 2 (BRSII or BRII) resistance gene.

FIG. 2 provides further map data with reference to the BRSII gene, including a SNP marker for the resistance trait.

FIGS. 3A and 3B provide a BestFit alignment of resistant and susceptible alleles of the BRSII markers (SEQ ID NOS: 2 and 1 respectively). Polymorphisms are indicated by asterisks.

FIGS. 4A through 4D provide a table providing pedigree and phenotypic data for progeny of the mapping population.

BRIEF DESCRIPTION OF THE SEQUENCES

SEQ ID NO: 1 represents the marker allele for *Orobanche* System 2 susceptibility.

SEQ ID NO: 2 represents the marker allele for *Orobanche* System 2 resistance.

SEQ ID NO: 3 and 4 represent probes used to identify the BRSII-susceptible and BRSII-resistant marker alleles at positions 105-106 of SEQ ID NO: 1 and 2.

SEQ ID NO: 5 and 6 represent forward and reverse primers, respectively, for amplifying marker alleles at positions 105-106 of SEQ ID NO: 1 and 2.

SEQ ID NO: 7 and 8 represent probes used to identify the BRSII-susceptible and BRSII-resistant marker alleles at position 142 of SEQ ID NO: 1 and 2.

SEQ ID NO: 9 and 10 represent reverse and forward primers, respectively, for amplifying marker alleles at position 142 of SEQ ID NO: 1 and 2.

DETAILED DESCRIPTION OF THE INVENTION

Although specific DNA sequences which encode proteins are generally well-conserved within a species, non-coding regions tend to accumulate polymorphism, and therefore can vary between individuals of the same species. Such regions provide the basis for numerous molecular genetic markers. In general, any differentially-inherited nucleic acid polymorphism that segregates among progeny is a potential molecular marker. The genomic variability can be of any origin, including insertions, deletions, duplications, repetitive elements, point mutations, recombination events, and the presence and sequence of transposable elements. Numerous methods for detecting molecular markers are also well-established.

Markers corresponding to genetic polymorphisms between members of a population can be detected by numerous methods, well-established in the art, such as restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP). The markers of the present invention are SNPs.

Molecular genetic markers can facilitate mapping and selection of agriculturally important traits. A molecular marker that demonstrates linkage disequilibrium with a desired phenotypic trait can be a useful tool for marker-assisted selection (MAS), providing a means for rapid identification of desirable individuals or lines. Introgression of preferred genes into a cultivar is also facilitated by MAS.

Components of the implementation of MAS may include: (i) the creation of a dense genetic map of molecular markers, (ii) the detection of statistical associations between marker and phenotypic variability, (iii) the definition of a set of desirable marker alleles, and (iv) the extrapolation of this information to the current set of breeding germplasm to enable marker-based selection decisions to be made.

In general, the identification of markers for MAS application involves the phenotyping of the trait(s) of interest and genotyping of the segregating population of progenies with polymorphic markers and genetic mapping of the desired trait. Details of mapping are described elsewhere herein. Polymorphic loci in the vicinity of the mapped trait are chosen as potential markers (typically, a marker locus closest to the locus of interest is a preferred marker). Linkage analysis is then used to determine which polymorphic marker allele sequence demonstrates a statistical likelihood of co-segregation with the desirable phenotype (thus, a "marker allele"). It is then possible to use this marker for rapid, accurate screening of plant lines for the marker allele without the need to grow the plants through their life cycle and await phenotypic evaluations. Furthermore, this permits genetic selection for the particular allele even when the molecular identity of the actual tolerance QTL is unknown. Tissue samples can be taken, for example, from the first leaf of the plant and screened with the appropriate molecular marker, and within days it is determined which progeny will advance. Use of linked markers also removes the impact of environmental factors that can influence phenotypic expression, and, unlike field evaluations, marker analysis can be done at any time of the year.

Plant breeders seek combinations of loci with genes for high yield and other desirable traits to develop improved varieties. Screening large numbers of samples by non-molecular methods (e.g., trait evaluation in sunflower plants) can be expensive, time-consuming, and unreliable. Use of the polymorphic markers described herein provides an effective method for selecting resistant varieties in breeding programs. When a population is segregating for multiple loci affecting one or multiple traits, e.g., multiple loci involved in tolerance, or multiple loci each involved in tolerance or resistance to different diseases, the efficiency of MAS compared to phenotypic screening becomes even greater, because all of the loci can be evaluated in the lab together from a single sample of DNA.

A specific application of MAS in plant breeding is to assist in efficient recovery of the recurrent parent genotype in backcross breeding. In marker-assisted backcrossing of specific markers (and associated QTL) from a donor source, e.g., to an elite genetic background, one selects among backcross progeny for the donor trait and then uses repeated backcrossing to the elite line to reconstitute as much of the elite background's genome as possible.

Thus, the markers and methods of the present invention can be utilized to guide marker-assisted selection or breeding of sunflower lines with the desired complement of allelic forms of chromosome segments associated with superior agronomic performance. Certain embodiments of the invention encompass the nucleic acids corresponding to the markers, including but not limited to probes, amplification primers, and amplification products, all of which are useful in the genotyping of plants, as well as the use of said nucleic acids for genome walking to identify additional sequences or contigs adjacent to the marker(s) for identification of additional or alternative sequence polymorphism/s for use in marker-assisted selection. More generally, these markers are useful in the saturation of a sunflower genetic map.

The present invention also extends to a method of breeding parent plants to form progeny sunflower plants and to these progeny plants, per se. Methods of crossing and growing sunflower plants are well within the ability of those of ordinary skill in the art. Resulting progeny can be assayed for alleles associated with resistance and the desired progeny can be selected. Such progeny plants or seed can be sold commercially for sunflower production, used for food, processed to obtain a desired constituent, or further utilized in subsequent rounds of breeding. At least one of the parent plants is a plant of the present invention in that it comprises at least one of the allelic forms of the markers of the present invention, such that the progeny are capable of inheriting the allele.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite x exotic sunflower lines by subjecting the segregating progeny to MAS to maintain major yield alleles, along with the resistance marker alleles herein.

In addition, "positional gene cloning" uses the proximity of a tolerance marker to physically define an isolated chromosomal fragment containing a tolerance QTL. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, infra.

Certain linkage maps of the sunflower genome are available; see, for example, Tang, et al., "PCR-multiplexes for a genome-wide framework of simple sequence repeat marker loci in cultivated sunflower," (2003) *Theor. Appl. Genet.* 107: 6-19; Yu, et al., "Towards a Saturated Molecular Genetic Linkage Map for Cultivated Sunflower," (2003) *Crop Science* 43:367-387; Lai, et al., "Identification and Mapping of SNPs from ESTs in Sunflower," (2005) *Theor. Appl. Genet.* 111: 1532-1544; Kusterer, et al., "Molecular Mapping of the Fertility Restoration Locus Rf1 in Sunflower and Development of Diagnostic Markers for the Restorer Gene," (2005) *Euphytica* 143:35-42; Pérez-Vich, et al., "Molecular Mapping of Nuclear Male Sterility Genes in Sunflower," (2005) *Crop Sci.* 45:1851-1857; and Chen, et al., "Molecular Mapping of a Nuclear Male-Sterility Gene in Sunflower using TRAP and SSR Markers," (2006) *Theor. Appl. Gen.* 113(1): 122-127. A marker may be linked to one or more loci of interest, for example a single gene, a quantitative trait locus (QTL), or another marker.

The majority of genetic markers rely on one or more properties of nucleic acids for their detection. For example, some techniques for detecting genetic markers utilize hybridization of a probe nucleic acid to nucleic acids corresponding to the genetic marker. Hybridization formats include, but are not limited to, solution phase, solid phase, mixed phase, or in situ hybridization assays. Restriction fragment length polymorphism (RFLP) markers are detected by hybridizing a probe to restriction-enzyme-digested genomic DNA. The probe is typically a sub-fragment (or a synthetic oligonucleotide corresponding to a sub-fragment) of the nucleic acid to be detected. The restriction enzyme is selected to provide restriction fragments of at least two alternative (or polymorphic) lengths in different individuals, and will often vary from line to line. Determining which restriction enzyme/s produce informative fragments for each combination of individuals is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target, followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling markers is readily achieved such as by the use of labeled PCR primers to marker loci.

The hybridized probe is then detected, most typically by autoradiography or other similar detection technique (e.g., fluorography or liquid scintillation counter). Examples of specific hybridization protocols are widely available in the art, see, e.g., Berger and Kimmel (1987) *Guide to Molecular Cloning Techniques, Methods in Enzymology vol.* 152, Academic Press, Inc., San Diego ("Berger"); Sambrook, et al., (2001) *Molecular Cloning-A Laboratory Manual,* 3$^{rd}$ ed. Vols. 1-3, Cold Spring Harbor Laboratory, Cold Spring Harbor ("Sambrook"); and Ausubel, et al., (eds) (supplemented through 2001) *Current Protocols in Molecular Biology,* John Wiley and Sons, Inc. ("Ausubel").

"Amplified variable sequences" refers to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis, et al., (1987) U.S. Pat. No. 4,683,202; *PCR Protocols, A Guide to Methods and Applications* (Innis, et al., eds.) Academic Press Inc., San Diego Academic Press Inc. San Diego, Calif. (1990) (Innis); Arnheim & Levinson (Oct. 1, 1990) *C&EN* 36-47; *The Journal Of NIH Research* (1991) 3:81-94; Kwoh, et al., (1989) *Proc. Natl. Acad. Sci. USA* 86:1173; Guatelli, et al., (1990) *Proc. Natl. Acad. Sci. USA* 87:1874; Lomell, et al., (1989) *J. Clin. Chem* 35:1826; Landegren, et al., (1988) *Science* 241: 1077-1080; Van Brunt (1990) *Biotechnology* 8:291-294; Wu and Wallace, (1989) *Gene* 4:560; Barringer, et al., (1990) *Gene* 89:117; and Sooknanan and Malek (1995) *Biotechnology* 13:563-564. Improved methods of cloning in vitro amplified nucleic acids are described in Wallace, et al., U.S. Pat. No. 5,426,039. Improved methods of amplifying large nucleic acids by PCR are summarized in Cheng, et al., (1994) *Nature* 369:684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as primers, e.g., in amplification reactions and for use as nucleic acid sequence probes, are typically synthesized chemically according to the solid phase phosphoramidite triester method described by Beaucage and Caruthers (1981) *Tetrahedron Lett.* 22:1859, or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli, et al., (1990) *Proc Natl Acad Sci USA* 87:1874). By mimicking the retroviral strategy of RNA replication by means of cDNA intermediates, this reaction accumulates cDNA and RNA copies of the original target.

Mapping of Marker Loci

Multiple experimental paradigms have been developed to identify and analyze molecular markers. In general, these paradigms involve crossing one or more parental pairs, which can be, for example, a single pair derived from two inbred strains, or multiple related or unrelated parents of different inbred strains or lines, which exhibit different characteristics relative to the phenotypic trait of interest. The parents and a population of progeny are genotyped for marker loci and phenotypically evaluated for the trait of interest. In the context of the present invention, the parental and progeny plants are genotyped for the BRSII marker or homologues, or alternative markers linked to the BRSII marker, and evaluated for resistance to *Orobanche*. Markers associated with resistance are identified based on significant statistical correlations between the marker genotype(s) and the phenotypes of the evaluated progeny plants. Numerous methods for determining whether markers are genetically linked to a gene associated with resistance to *Orobanche* are known to those of skill in the art and include, e.g., interval mapping (Lander and Botstein (1989) *Genetics* 121:185), regression mapping (Haley and Knott (1992) *Heredity* 69:315) and MQM mapping (Jansen (1994) *Genetics* 138:871). See also, U.S. Pat. Nos. 6,399,855 and 6,368,806.

Two types of markers often used in marker assisted selection protocols are the simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two- or three-base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. Dinucleotide repeats have been found in higher plants (Condit and Hubbell (1991) *Genome* 34:66).

SSR genomic variability is inherited, multiallelic, codominant and reproducibly detectable, making SSRs well suited for use as molecular genetic markers. The proliferation of increasingly sophisticated amplification-based detection techniques (e.g., PCR) provides a variety of sensitive methods for the detection of nucleotide sequence heterogeneity. Primers (or other types of probes) are designed to hybridize to conserved regions that flank the SSR domain, resulting in the amplification of the variable SSR region. The various amplicons generated from an SSR region have characteristic and reproducible sizes. The different-sized SSR amplicons observed from two homologous chromosomes in an individual, or from different individuals in the plant population, are generally termed "marker alleles." As long as there exist at least two SSR alleles that produce PCR products with at least two different sizes, the SSR can be employed as a marker. SSR markers may be developed from genomic DNA or ESTs (expressed sequence tags).

Markers that rely on single nucleotide polymorphisms (SNPs) are also well known in the art. A SNP results when a single nucleotide (A, T, C, or G) in the genomic sequence is altered, or an insertion/deletion occurs. The SNP may or may not result in a functional gene change. Various techniques have been developed for the detection of SNPs, including the allele specific hybridization method (ASH; see, e.g., Coryell, et al., (1999) "Allele specific hybridization markers for soybean," *Theor. Appl. Genet.* 98:690-696). Refinements of SNP analysis and adaptations for use in high-throughput systems are known to those of skill in the art; see, for example, Shirasawa, et al., (2006) *Theor. Appl. Genet.* 113(1):147-155; Giancola, et al., (2006) *Theor. Appl. Genet.* 112(6):1115-1124. An SSR marker may serve as a first step in development of a SNP marker; see, Brooks, et al., (2006) *Crop Sci.* 46(4):1467-1470. SSR and SNP markers may be used in combination; see, Gilson, et al., (2006) *Transgenic Res.* 15(6):785-786. SNP analysis of promoter sequences has been reported (Schwarz, et al., (2003) *J. Agr. Food Chem.* 51(15):4263-4267).

Additional types of molecular markers are also widely used, including restriction fragment length polymorphism (RFLP), amplified fragment length polymorphism (AFLP), randomly amplified polymorphic DNA (RAPD), and isozyme markers. A wide range of protocols are known to those of skill in the art for detecting this variability, and these protocols are frequently specific for the type of polymorphism they are designed to detect, including, for example, PCR amplification, single-strand conformation polymorphisms (SSCP) and self-sustained sequence replication (3SR; see, Chan and Fox (1999) "NASBA and other transcription-based amplification methods for research and diagnostic microbiology," *Reviews in Medical Microbiology* 10:185-196).

Regardless of their molecular nature, e.g. whether a marker is an SSR, SNP, RFLP, or other type, markers are typically strain-specific; that is, a particular marker is defined relative to the parental lines of interest. For each marker locus, resistance and susceptibility alleles are identified for each pair of parental lines. Following correlation of specific alleles with resistance or susceptibility in the parental lines, the marker can be utilized to identify progeny with genotypes that correspond to the desired phenotype.

Linkage of a molecular marker to a locus of interest is measured as a recombination frequency, which establishes distance (in centiMorgans, cM) between landmarks on the genetic map. Physical distance between loci is measured in basepairs, e.g., the number of kilobasepairs (kb) or megabasepairs (Mbp) that two loci are separated from each other on a chromosome. In general, the closer two loci (e.g., a SNP marker and a QTL) are on the genetic map, the closer they lie to each other on the physical map. While relative genetic distance is generally proportional to the physical distance between loci, imprecise correlation between cM and physical distance can result from variation in recombination frequencies for different chromosomal regions. Some chromosomal regions are recombinational "hot spots," while other regions do not show any recombination, or demonstrate only rare recombination events. In general, the closer a marker is to the locus of interest, whether measured in terms of recombination or of physical distance, the better it serves to signal the desired selectable trait.

It is the goal of the plant breeder to enrich the plant population for individuals with desired traits, leading ultimately to improved agricultural productivity. It is known that specific chromosomal loci (or intervals) that can be mapped in an organism's genome may correlate with particular quantitative phenotypes. Such loci are termed quantitative trait loci, or QTL. The plant breeder can advantageously use molecular markers to identify desired individuals by identifying marker alleles that show a statistically significant probability of co-segregation with a desired phenotype, manifested as linkage disequilibrium. By identifying a molecular marker or cluster of molecular markers that co-segregates with a quantitative trait, the breeder is thus identifying a QTL. Multiple experimental paradigms have been developed to identify and analyze QTL (see, e.g., Jansen (1996) *Trends Plant Sci* 1:89). The majority of published reports on QTL mapping in crop species have been based on the use of the bi-parental cross (Lynch and Walsh (1997) *Genetics and Analysis of Quantitative Traits*, Sinauer Associates, Sunderland). By identifying and selecting a marker allele (or desired alleles from multiple markers) associating with the desired phenotype, the plant breeder is able to rapidly select for the desired phenotype.

This process is called marker-assisted selection, or MAS. The more molecular markers that are placed on the genetic map, the more potentially useful that map becomes for conducting MAS.

Numerous statistical methods for determining whether markers are genetically linked to a locus of interest are known to those of skill in the art and include, e.g., standard linear models, such as ANOVA or regression mapping (Haley and Knott (1992) *Heredity* 69:315), maximum likelihood methods such as expectation-maximization algorithms, (e.g., Lander and Botstein (1989) "Mapping Mendelian factors underlying quantitative traits using RFLP linkage maps," *Genetics* 121:185-199; Jansen (1992) "A general mixture model for mapping quantitative trait loci by using molecular markers," (1993) *Theor. Appl. Genet.*, 85:252-260; Jansen "Maximum likelihood in a generalized linear finite mixture model by using the EM algorithm," *Biometrics* 49:227-231; Jansen (1994) "Mapping of quantitative trait loci by using genetic markers: an overview of biometrical models," In J. W. van Ooijen and J. Jansen (eds.), *Biometrics in Plant breeding: applications of molecular markers*, pp. 116-124, CPRO-DLO Netherlands; Jansen (1996) "A general Monte Carlo method for mapping multiple quantitative trait loci," *Genetics* 142: 305-311; and Jansen and Stam (1994) "High Resolution of quantitative trait into multiple loci via interval mapping," *Genetics* 136:1447-1455). Exemplary statistical methods include single point marker analysis, interval mapping (Lander and Botstein (1989) *Genetics* 121:185), composite interval mapping, penalized regression analysis, complex pedigree analysis, MCMC analysis, MQM analysis (Jansen (1994) *Genetics* 138:871), HAPLO-IM+ analysis, HAPLO-MQM analysis, HAPLO-MQM+ analysis, Bayesian MCMC, ridge regression, identity-by-descent analysis, and Haseman-Elston regression, any of which are suitable in the context of the present invention. Additional details regarding alternative statistical methods applicable to complex breeding populations which can be used to identify and localize QTLs are described in: U.S. Pat. No. 6,399,855 by Beavis, et al., "QTL Mapping in Plant Breeding Populations" and WO2001/049104 by Jansen, et al., "MQM Mapping Using Haplotyped Putative QTL-Alleles: A Simple Approach for Mapping QTLs in Plant Breeding Populations." These approaches are computationally intensive and are usually performed with the assistance of a computer based system and specialized software. Appropriate statistical packages are available from a variety of public and commercial sources, and are known to those of skill in the art.

There is a need in the art for improved sunflower germplasm that is resistant to *Orobanche cumana*. There is a need in the art for the identification of molecular markers that are linked to *Orobanche cumana* resistance loci in order to facilitate MAS. Such markers can be used to select individual plants and plant populations that show favorable marker alleles which can then be employed to select the resistant phenotype. Alternatively, the markers may be used to counterselect plant or plant populations that are susceptible to *Orobanche cumana*. The present invention provides compositions and methods that meet these needs and provide other advantages.

Methods for identifying sunflower plants or germplasm that display resistance, improved resistance, or susceptibility to *Orobanche cumana* are provided. Methods of making sunflower plants or germplasm that are resistant or have improved resistance to *Orobanche cumana* are also provided, e.g., where resistant plants are created through introgression of desired resistance marker alleles (e.g., marker assisted selection) and/or by transgenic production methods. The plants or germplasm produced by the methods of the invention are also an aspect of the invention. Systems for identifying plants and germplasm predicted to have resistance, improved resistance, or susceptibility to *Orobanche cumana* are also a feature of the invention, as are kits that facilitate the methods of the invention.

In certain embodiments, the invention provides methods for identifying a first sunflower plant that has resistance, improved resistance, or susceptibility to *Orobanche cumana*. In the methods, at least one allele of a marker locus that is associated with the resistance, improved resistance, or susceptibility phenotype is detected in the first sunflower plant. The marker locus can be BRSII.

Typically, the closely-linked locus displays a genetic recombination frequency of less than about 10% with reference to the marker locus. In desirable embodiments, the linked locus displays a genetic recombination frequency of 9%, 8%, 7%, 6%, 5%, 4%, 3%, 2%, 1%, 0.75%, 0.5% or 0.25%, or less.

Desirably, plants are identified that have at least one favorable allele that positively correlates with resistance or improved resistance. Optionally, two, three or more favorable allele(s) are identified in, or introgressed into, the plant. Any suitable technique can be used to assay the resistance or susceptibility of a sunflower plant to *Orobanche cumana*. For example, resistance can be scored in a field location known to harbor *Orobanche* seeds, or the level of resistance can be scored using controlled greenhouse or nursery conditions. Methods of screening are described in detail in WO 2003/073837.

Any of a variety of molecular methods can be used to detect a marker allele. For example, an allelic form of a polymorphic simple sequence repeat (SSR) can be detected by an amplification-based technology such as PCR. Alternatively, a single nucleotide polymorphism (SNP) marker allele can be detected by an amplification step followed by an allele specific hybridization assay (ASH). In these and other amplification-based detection methods, the marker locus or a portion thereof is amplified (e.g., via PCR, LCR or transcription using a nucleic acid isolated from a plant of interest as a template) and the resulting marker amplicon is detected.

In one example, an amplification primer or amplification primer pair (e.g., a primer pair provided as SEQ ID NOS: 5 and 6) is admixed with genomic nucleic acid isolated from the first sunflower plant, wherein the primer or primer pair is complementary or partially complementary to at least a portion of the marker locus, and is capable of initiating DNA polymerization by a DNA polymerase using the sunflower genomic nucleic acid as a template. The primer or primer pair (e.g., a primer pair that amplifies the BRSII marker locus) is extended in a DNA polymerization reaction having a DNA polymerase and a template genomic nucleic acid to generate at least one amplicon. In any case, data representing the detected allele(s) can be transmitted (e.g., electronically or via infrared, wireless or optical transmission) to a computer or computer readable medium for analysis or storage.

It will be appreciated that the ability to identify a favorable marker locus that correlates with resistance to *Orobanche* provides a method for selecting plants with a favorable resistance trait. That is, any plant that is identified as comprising a desired marker locus can be selected for, while plants lacking that locus, or having a locus that is negatively correlated with resistance, can be selected against.

Thus, in one method, subsequent to identification of a favorable marker locus, the methods include selecting the first sunflower plant, or selecting progeny of the first plant. Furthermore, the selected first sunflower plant can be crossed with a second sunflower plant (e.g., an elite or exotic sunflower, depending on characteristics that are desired in the progeny). Similarly, if an allele is correlated with resistance to *Orobanche*, a method may comprise introgressing the allele into a second sunflower plant. Desirably, the second sunflower plant displays less resistance to *Orobanche* than the first sunflower plant, while the introgressed sunflower plant displays an increased tolerance to *Orobanche* as compared to the second plant. In some embodiments, an elite sunflower plant is used as the second plant for introgression. An introgressed sunflower plant or germplasm produced by any of the methods provided herein is also a feature of the present invention.

Transgenic approaches can also be used to produce *Orobanche* resistant sunflower plants or germplasm. For example, methods of producing a sunflower plant having improved resistance to *Orobanche* can include introducing an exogenous nucleic acid into a target sunflower plant, wherein the exogenous nucleic acid is derived from a genomic nucleotide sequence that is closely linked to a favorable marker locus associated with improved resistance to *Orobanche*. The marker locus can be BRSII, and/or a genetic locus linked thereto.

Any of a variety of methods can be used to provide the exogenous nucleic acid. In one method, the nucleotide sequence is isolated by positional cloning, and is identified by linkage to the favorable allele. The precise composition of the exogenous nucleic acid can vary; in one embodiment, the exogenous nucleic acid corresponds to an open reading frame (ORF) that encodes a polypeptide that, when expressed in a sunflower plant, results in the sunflower plant having improved resistance to *Orobanche*.

Systems for identifying a sunflower plant predicted to have resistance, improved resistance, or susceptibility to *Orobanche* are also a feature of the invention. Typically, the system can include (a) a set of marker probes or primers configured to detect at least one favorable allele of a marker locus associated with resistance to *Orobanche*, wherein the marker locus can be BRSII or a genetic locus linked thereto; (b) a detector that is configured to detect one or more signal outputs from the set of marker probes or primers, or amplicon thereof, thereby identifying the presence or absence of the allele; and (c) system instructions that correlate the presence or absence of the favorable allele with the predicted resistance or susceptibility. In some embodiments, the set of marker probes or primers comprises nucleotide sequences provided in SEQ ID NOS: 3-6.

The precise configuration of the detector will depend on the type of label used to detect the marker allele. Typical embodiments include light detectors, radioactivity detectors, and the like. Detection of a light emission (or multiple light emissions) or other probe label is indicative of the presence or absence of a marker allele. Similarly, the precise form of the instructions can vary depending on the components of the system, e.g., they can be present as system software in one or more integrated unit of the system, or can be present in one or more computers or computer readable media operably coupled to the detector. In one typical embodiment, the system instructions include at least one look-up table that includes a correlation between the presence or absence of the favorable allele and predicted resistance or improved resistance.

The system can be comprised of separate elements or can be integrated into a single unit for convenient detection of marker alleles and for performing marker-trait correlations.

The system can also include a sample such as genomic DNA, amplified genomic DNA, cDNA, amplified cDNA, RNA, or amplified RNA from sunflower or from a selected sunflower plant tissue.

Unless otherwise defined, all technical and scientific terms used herein have the same meaning as commonly understood by one of ordinary skill in the art to which this invention belongs. Unless mentioned otherwise, the techniques employed or contemplated herein are standard methodologies well known to one of skill in the art. The materials, methods and examples are illustrative only and not limiting of the scope of the invention.

In the context of this disclosure, a number of terms will be used. In order to provide a clear and consistent understanding of the specification and claims, including the scope to be given such terms, the following definitions are provided.

"Allele" refers to one of two or more nucleotide sequences that may occur at a specific chromosomal locus. A heterozygous diploid individual has two different forms of a sequence, or allele, at corresponding loci of the chromosome pair. A homozygous diploid individual has two copies of the same allele at corresponding loci of homologous chromosomes.

A "favorable allele" may be the allele at a particular locus that confers, or contributes to, an agronomically desirable phenotype. In other circumstances, a "favorable allele" may be one which allows identification of plants with negative agronomic traits, such as disease susceptibility.

An allele "positively" correlates with a trait when presence of the allele is an indicator that the desired trait or trait form will occur in a plant comprising that allele. An allele "negatively" correlates with a trait when presence of the allele is an indicator that a desired trait or trait form will not occur in a plant comprising the allele.

"Allele frequency" refers to the frequency at which an allele is present at a locus within an individual, within a line, or within a population of lines. For example, for an allele "A," diploid individuals of genotype "AA," "Aa," or "aa" have allele frequencies of 1.0, 0.5, or 0.0, respectively.

The term "associated with" or "associated" in the context of this invention refers to, for example, a nucleic acid and a phenotypic trait that are in linkage disequilibrium, i.e., the nucleic acid and the trait are found together in progeny plants more often than if the nucleic acid and phenotype segregated separately.

"Broomrape", "*Orobanche cumana*" "*Orobanche cumana* Wallr.", "*O. cernua* Loefl", "*Orobanche*", and "*O. cumana*" are herein used interchangeably to refer to the described parasitic weed and its races.

The term "centiMorgan" means a unit of measure of recombination frequency. One centiMorgan represents a 1% chance that a marker at a first genetic locus will, in a single generation, be separated from a marker at a second locus due to crossing over.

"Cytoplasmic Male Sterile" or "CMS": A sunflower line that produces no viable pollen is called male sterile. Cytoplasmic male sterility is inherited maternally, i.e., the male sterile plant is used as the female parent in a cross with pollen from another sunflower. CMS lines are produced by crossing a maintainer line to a sunflower plant with the cytoplasmic male sterility trait, and then backcrossing with the maintainer line until a male sterile line that is homologous to the maintainer line in all other respects is developed. CMS lines are also referred to as female lines.

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a reference point on a genetic map, relative to surrounding genetic markers on the same linkage group, where a specified marker can be found. In contrast, a physical map of the genome refers to absolute distances (for example, measured in base pairs or isolated and overlapping contiguous genetic fragments, or contigs). A physical map of the genome does not take into account the genetic behavior (e.g., recombination frequencies) of various chromosome segments.

The term "genetically linked" refers to genetic loci that are in linkage disequilibrium and statistically determined not to assort independently. Genetically linked loci assort dependently from 51% to 99% of the time or any whole number value there between, preferably at least 60%, 70%, 80%, 90%, 95% or 99%.

The term "homogeneity" indicates that members of a group have the same genotype at one or more specific loci. The term "heterogeneity" indicates that individuals within the group differ in genotype at one or more specific loci.

The term "homologous" refers to nucleic acid sequences that are derived from a common ancestral gene through natural or artificial processes (e.g., are members of the same gene family), and thus typically share sequence similarity. Homologous nucleic acids often have sufficient sequence identity that one of the sequences or its complement is able to selectively hybridize to the other under stringent hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have at least about 80% sequence identity, often at least 90% sequence identity, and may have 95%, 97%, 98%, 99%, or 100% sequence identity with each other. A nucleic acid that exhibits at least some degree of homology to a reference nucleic acid can be unique or identical to the reference nucleic acid or its complementary sequence.

The term "host cell" means a cell which contains a heterologous nucleic acid, such as a vector, and supports the replication and/or expression of the nucleic acid. Host cells may be prokaryotic cells such as E. coli, or eukaryotic cells such as yeast, insect, amphibian, or mammalian cells. Preferably, host cells are plant cells. In the context of the invention, one particularly preferred host cell is a sunflower cell.

The term "interval" refers to a continuous linear span of chromosomal DNA with termini defined by and including molecular markers.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction."

The term "introgression" refers to the transmission of a desired allele of a genetic locus from one genetic background to another. For example, introgression of a desired allele at a specified locus can occur via a sexual cross between two plants, where at least one of the plants has the desired allele within its genome. The allele is introgressed into the progeny. In another example, transmission of an allele can occur by recombination between two donor genomes in vitro, e.g., in a fused protoplast, where at least one of the donor protoplasts has the desired allele in its genome. The desired allele can be, e.g., a transgene or a selected allele of a marker or quantitative trait locus.

The term "isolated" refers to material, such as a nucleic acid or a protein, which is substantially free from components that normally accompany or interact with it in its naturally-occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally-occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

"Line" means a group of plants that are genetically homogeneous and display little variation between individuals, generally as a result of several generations of self-pollination. Also, a line can include a group of plants vegetatively propagated from a single parent plant, using tissue or cell culture technique.

The term "linkage disequilibrium" refers to a non-random segregation of genetic loci. This implies that such loci are in sufficient physical proximity along a length of a chromosome that they tend to segregate together, i.e., with a frequency greater than would occur at random.

The terms "marker", "molecular marker", and "marker locus" refer to a nucleotide sequence or encoded product thereof (e.g., a protein) used as a point of reference when identifying a linked locus, such as a quantitative trait locus (QTL). A marker can be derived from genomic nucleotide sequence or from expressed nucleotide sequences or from an encoded polypeptide. The term may also refer to nucleic acid sequences complementary to, or flanking, the marker sequences, such as nucleic acids used as probes or primer pairs capable of amplifying the marker sequence. Such a nucleic acid sequence or molecule that can be used to identify the presence of a marker locus, e.g., a nucleic acid probe that is complementary to a marker locus sequence, may also be referred to as a "marker probe." Alternatively, in some aspects, a marker probe refers to a probe of any type that is able to distinguish (i.e., genotype) the particular allele that is present at a marker locus.

The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the terms can additionally or alternatively include analogs of naturally-occurring nucleotides having the essential nature of natural nucleotides in that they hybridize to single-stranded nucleic acids in a manner similar to that of naturally-occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, for example, a cDNA and an mRNA encoded by the genomic sequence, as well as to that genomic sequence.

"Plant or plant parts" refers to plant cells, plant protoplasts, plant cell tissue cultures from which plants can be regenerated, plant calli, plant clumps, and plant cells that are intact in plants or parts of plants such as embryos, pollen, ovules, flowers, leaves, husks, stalks, roots, root tips, anthers, seed and seed meal, and the like.

The term "quantitative trait locus" or "QTL" refers to a polymorphic genetic locus with at least two alleles that differentially reflect the expression of a continuously distributed phenotypic trait.

For the purpose of this invention, "resistance", "broomrape resistance" or "*Orobanche* resistance" is defined as a genetically controlled attribute of sunflower plants that prevents a parasitic broomrape plant from attaching to a sunflower plant and completing its life cycle through the reproductive (seed-bearing) stage. The resistance may result from one or more of several plant-parasite responses, including but not necessarily limited to: (1) lack of sufficient broomrape seed germination stimulus from the sunflower plant (assumed to be a chemical root exudate); (2) blockage of broomrape haustorial penetration of the sunflower root surface; or (3) blockage of broomrape haustorial connection to the vascular system of the sunflower plant.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868.

"Restorer line" means a line possessing the gene or genes to restore male fertility or pollen viability to a sunflower hybrid or inbred line having a maternal cytoplasm that conditions male sterility. This term is also discussed in the literature. See, for example, Fick, "Breeding and Genetics," in *Sunflower Science and Technology* 279-338 (J. F. Carter, ed., 1978), the contents of which are incorporated herein by reference.

"Selection" means the extraction of a desired phenotype from a broad, genetically heterogeneous breeding pool, commonly termed a population. Individual plants within the population are selected for preferred manifestations of such traits as plant morphology, flower morphology, insect or disease resistance, maturity and yield.

The term "simple sequence repeat" or "SSR" refers to a type of molecular markers (also known as microsatellite) based on short sequences of nucleotides (2-6 units in length) that are repeated in tandem. For example, a di-nucleotide repeat could be GAGAGAGA and a tri-nucleotide repeat could be ATGATGATGATG. It is believed that when DNA is being replicated, errors occur in the process and extra sets of these repeated sequences are added to the strand. Over time, these repeated sequences vary in length between one cultivar and another. An example of an allelic variation in SSRs would be: Allele A: GAGAGAGA (4 repeats of the GA sequence) and Allele B: GAGAGAGAGAGA (6 repeats of the GA sequence). These variations in length are easy to trace in the lab and allow tracking of genotypic variation in breeding programs.

The term "single nucleotide polymorphism" or "SNP" refers to a single-nucleotide alteration in the genomic sequence. This may occur when a single adenine, thymine, cytosine, or guanine (represented by A, T, C, or G) is changed to any one of the other four nucleotides, or when a single nucleotide is inserted or deleted. The SNP may or may not result in a functional gene change.

The term "transgenic plant" refers to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those which are created by sexual or asexual propagation from the initial transgenic organism or cell and retain the heterologous nucleic acid. The term "transgenic" as used herein does not encompass the alteration of the genome (chromosomal or extra-chromosomal) by conventional plant breeding methods (i.e., crosses) or by naturally-occurring events such as random cross-fertilization, non-recombinant viral infection, non-recombinant bacterial transformation, non-recombinant transposition, or spontaneous mutation.

"Variety" or "cultivar" refers to a group of plants within the species (e.g., *Helianthus annuus*) which share certain constant characteristics that separate them from the typical form and from other possible varieties within that species.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant. Thus the term "selfed" in a breeding program refers to self-pollination and the term "crossed" refers to cross-pollination.

Sunflowers have a head-type inflorescence with sterile ray flowers and perfect (having both stamen and pistil) disc flowers. In its wild state, the sunflower has been self-sterile or self-incompatible so it is a highly cross-pollinating crop that depends largely on honeybees or other insects for pollination. Most production areas do not have a sufficient bee population to adequately pollinate the crop. This has resulted in breeder selection for self-compatibility or self-fertility which increases the yield of seed when few bees are present.

A sunflower breeding population should be substantially homogenous and reproducible to be useful in either further breeding or the development of a commercial cultivar. There are a number of analytical methods available to determine the phenotypic stability of a sunflower population.

The oldest and most traditional method of analysis is the observation of phenotypic traits. The data are usually collected in field experiments over the life of the sunflower plants to be examined. Phenotypic characteristics most often are observed for traits associated with seed yield, seed oil content, seed protein content, fatty acid composition of oil, glucosinolate content of meal, growth habit, lodging resistance, plant height, shattering resistance, etc. Other phenotypic characteristics commonly observed include resistance to disease or insects, and tolerance to herbicides.

It has been found that the compositions and methods of the present invention can be useful in identifying novel lines of sunflowers resistant to *Orobanche cumana*.

An *Orobanche* seed near the root zone of a susceptible variety will germinate, form a haustorium on the susceptible plant's root and complete its life cycle by drawing substrate from the host plant, thereby causing severe detriment to the host plant's growth and yield. See, for example, Dominguez, (1996) *Plant Breed.* 115:203-204; Ish-Shalom-Gordon, et al., (1993) *Phytopathology* 83:1250-1252; Kirichenco, et al., (1987) *Plant Breed. Abstr.* 57:1392; Melero-Vara, et al. (2000), *Helia* 23:45-56; and Sukno, et al., (1999)*Crop Sci.* 39:674-678). System I resistance to *Orobanche cumana* results in failure of an *Orobanche* seed in the root zone of a resistant variety to infect the host plant. This form of resistance is represented in sunflower line U00S9LM and ATCC Accession # PTA-3793.

Unlike the case of System 1 resistance, a seed of *Orobanche cumana* in the root zone of sunflower plants that carry the System 2 resistance gene will germinate, penetrating the host root tissues and forming a haustorium. Broomrape shoots will begin to develop underground. However, for sunflower plants with the System 2 resistance gene, the invading *Orobanche* plant will wither and die before it emerges from the soil, unable to complete its life cycle on the resistant plant's root system. This form of resistance is represented in sunflower line 8556UG and ATCC Accession # PTA-3792; see, WO 2003/073837. In certain embodiments the present invention provides molecular markers for a gene that provides System 2 resistance to *Orobanche cumana*.

A third mechanism combines the sources of resistance of both systems to create a stronger resistance. This form of resistance is represented in sunflower hybrid 01UL2365 and ATCC Accession #PTA-3791. Broomrape resistance is strengthened by combining the System 2 resistance trait with other resistance genes.

In the past, breeders have had to rely on a bioassay to select resistant plants, looking for live broomrape within a radius of 50 cm around each plant and checking underground for any broomrape shoots attached to the root system. This is a very tedious method and may be inaccurate due to environmental effects. A molecular marker associated with the resistance allele of the System 2 resistance gene would allow breeders to more rapidly and reliably select resistant plants during the breeding process.

In certain embodiments the present invention provides molecular markers for System 2 resistance to *Orobanche cumana*. No molecular markers have previously been available for identifying or differentiating *Orobanche* System 2 resistance in sunflower. Sunflower breeders have had to rely on field observations when incorporating *Orobanche* System 2 resistance genes into their breeding populations. The novel molecular markers facilitate the efforts of sunflower breeders. For example, use of the markers allows breeders to:

1) Differentiate among plants within a segregating breeding population in order to identify those which carry the System 2 resistance gene.
2) Breed System 2 resistance into elite inbred lines that previously contained little or no resistance to *Orobanche*, thereby enhancing the diversity of sunflower products available to growers in areas infested with *Orobanche*.
3) Combine the System 2 gene with other resistance genes, to develop plants that contain both System 1 and System 2 resistance and thereby provide a resistance combination that is superior to either System 1 or System 2 resistance alone.
4) Combine the System 2 gene with genes that provide other useful traits, such as resistance to other parasites or diseases that affect sunflower, or herbicide tolerance.
5) Create new commercial products that may be used to deplete existing *Orobanche* seed banks in the soil profile and limit new seed deposits of *Orobanche* in a cropping system.
6) Identify regions and/or gene clusters in the sunflower genome that give rise to *Orobanche* resistance in sunflower and clone useful genes from these loci for further marker development or development of novel transgene constructs that may be used to develop transgenic sunflowers with resistance to *Orobanche*.

The compositions and methods of the present invention can assist in reproducibly creating sunflower lines that express the *Orobanche* resistance trait within a consistent phenotypic background exhibiting one or more desirable traits such as high seed yield, early maturity, drought tolerance, cold tolerance, suitable seed protein content and amino acid composition, dwarfism, resistance to lodging, resistance to insects or diseases caused by bacteria, fungi, or viruses, and tolerance to herbicide treatment.

Hybrid Development in Sunflower

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent, since only the female provides cytoplasm to the fertilized seed. CMS may be derived from sunflower lines well known in the art and publicly available such as CMS HA89 (USDA). The source of CMS HA89 is the material of Leclercq, "Cytoplasmic Sterility in the Sunflower," (1969) *Ann. Amelior Plant* 19:99-106.

CMS plants are fertilized with pollen from another plant that is not male-sterile. Pollen from the second plant may or may not contribute genes that make the progeny plants male-fertile.

Cytoplasmic male sterile lines are traditionally developed by the backcrossing method in which desirable lines that have undergone inbreeding and selection for several generations are crossed initially to a plant with cytoplasmic male sterility. Thereafter the desirable inbred line is used as a recurrent parent in the backcrossing procedure. The final progeny will be genetically similar to the recurrent parent except that it will be male sterile.

Fertility restorer lines may be developed by using backcrossing to transfer a dominant restorer gene to an established inbred line with normal cytoplasm. If this procedure is used, selected plants must be crossed to a cytoplasmic male sterile line after each generation to determine if the fertility restorer genes are present. A more common procedure is self-pollination and selection of male fertile plants from commercial hybrids or planned crosses of parents having restorer genes in male sterile cytoplasm. This procedure does not require test crossing to a male sterile line during selection because the plants will be fully male fertile if the necessary restoring genes are present.

A suitable restorer line for CMS can be produced by crossing with any of the commonly available restorer lines, such as RHA274, RHA271, and RHA273 (USDA), or other lines possessing genes for restoration of male fertility. Lines and varieties thus derived which produce seed having broomrape resistance and which are true-breeding for at least the fertility restorer genes, can then be isolated by continuous self-pollination and crossed with the broomrape resistant CMS lines previously described.

Inbred Development in Sunflower

The use of male sterile inbreds is but one factor in the production of sunflower hybrids. The development of sunflower hybrids requires, in general, the development of homozygous inbred lines, the crossing of these lines, and the evaluation of the progeny. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines, and the hybrids from these crosses are evaluated for commercial potential.

Pedigree breeding is commonly used for the improvement of crops. Pedigree breeding starts with the crossing of two genotypes, each of which may have one or more desirable characteristics that is lacking in the other or which complements the other. If the two original parents do not provide all of the desired characteristics, additional parents can be included in the crossing scheme.

These parents are crossed in a simple or complex manner to produce an F1. An F2 population is produced by selfing one or several F1's or by intercrossing two F1's (i.e., sib mating). Selection of the best individuals may begin in the F2 population. Beginning in the F3, the best families, and the best individuals within the best families, are selected. Replicated testing of families (lines) can begin in the F4 generation to improve the effectiveness of selection for traits with low heritability. At an advanced stage of inbreeding (i.e., F6 and F7), the best lines or mixtures of phenotypically similar lines commonly are tested for potential release as new cultivars.

Improved varieties may also be developed through recurrent selection. A genetically variable population of heterozygous individuals is either identified or created by intercrossing several different parents. The best plants are selected based on individual superiority, outstanding progeny, and/or excellent combining ability. The selected plants are intercrossed to produce a new population in which further cycles of selection are continued.

The objective of commercial sunflower hybrid development programs is to develop new inbred lines that combine to produce hybrids with high yields and superior agronomic performance. Yield is the primary trait breeders seek. However, many other major agronomic traits are of importance in hybrid combinations and have an impact on yield or otherwise provide superior performance in hybrid combinations. Major objectives in sunflower breeding include improved seed yield, improved seed oil percentage or oil quality, earlier maturity, shorter plant height, uniformity of plant type, and disease or insect resistance. In addition, the lines per se preferably have acceptable performance for parental traits such as seed yields and pollen production, all of which affect ability to provide parental lines in sufficient quantity and quality for hybridization. These traits have been shown to be under genetic control and many if not all of the traits are affected by multiple genes.

Through breeding techniques, improved resistance to *Orobanche cumana* can be combined or "stacked" with any other desirable seed, agronomic, or insect- or disease-resistance trait. Examples of other desirable traits include, but are not limited to, altered seed oil profile or content, high seed yield, earlier maturity, drought tolerance, cold tolerance, increased seed protein content, modification of composition of amino acid content in seeds, dwarfism, resistance to lodging, resistance to insects or diseases caused by bacteria, fungi, or viruses, or tolerance to herbicide treatment.

The methods of the present invention find particular use in breeding programs with sunflower lines tolerant to sulfonylurea herbicide. Sulfonylurea herbicides have been found effective against parasitic weeds of sunflower such as dodder and *Orobanche* species (L. Garcia-Torres, et al., (1994) *Weed Research* 34:395-402).

Regeneration of Plants

This invention also relates to the parts of the plants disclosed herein, including plant cells, plant protoplasts, plant cell tissue cultures from which sunflower plants can be regenerated, plant calli, plant clumps, and plant cells that are intact in plants or parts of plants such as embryos, pollen, ovules, flowers, leaves, husks, stalks, roots, root tips, anthers, seed and seed meal, and the like.

The plants produced in accordance with the present invention may be regenerated from plant parts using known techniques. For instance, seeds from the plants of the present invention may be planted in accordance with conventional sunflower growing procedures. These plants will generate further seeds.

Sunflower plants may also be regenerated using tissue culture and regeneration. Culture of various cells and tissues of sunflower and regeneration of plants therefrom is known to those skilled in the art. For example, the propagation of sunflower by tissue culture is described in the following references: Henderson, et al, (1952) "The culture of normal sunflower stem callus.", *Am. J. Bot.* 39:444-451; Levine, M., (1951) "Response of fibrous roots of sunflower and tobacco tissue cultures to plant growth substances", *Bot. Gaz.* 112: 281-289; Henrickson, C. E., (1954) "The flowering of sunflower explants in aseptic culture", *Plant Physiol.* 29:536-538; and Sadhu, M. K., (1974) "Effect of different auxins on growth and differentiation in callus tissue from sunflower stem pith", *Indian J. Exp. Biol.* 12:110-111.

Vegetable Oil and Meal

The seed of the plants of this invention may be used for producing vegetable oil and meal. The seed of these varieties, the plant produced from such seed, the hybrid sunflower plant produced from the crossing of these varieties with other varieties, the resulting hybrid seed, and various parts of the hybrid sunflower plant can be utilized in the production of an edible vegetable oil or other food products in accordance with known techniques.

Units, prefixes, and symbols are denoted in their International System of Units (SI) accepted form. Unless otherwise indicated, nucleic acids are written left to right in 5' to 3' orientation; amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined herein are more fully defined by reference to the specification as a whole. Section headings provided throughout the specification are provided for convenience and are not limited to the various objects and embodiments of the present invention.

The following Examples are presented as specific illustrations of the claimed invention. It should be understood, however, that the invention is not limited to the specific details set forth in the Examples.

EXAMPLES

Example 1

Field Screening

Screening of the new source of breeding germplasm and inbred lines for resistance to broomrape was conducted over several years in the summer nursery at Ahmetbey, Luleburgaz-Kirklarli, Turkey. The nursery was artificially infested with seeds of new races of *O. cumana*. The soil infestation of the nursery was repeated every year. Screening was performed by planting 15 plants in a 4-meter row length for each selection of the breeding germplasm and inbred lines. Resistance to broomrape was assessed just prior to harvesting by removing plants from the ground and counting the number of sunflower plants with dead broomrape shoots attached to the sunflower root system below the soil surface. System 2 resistant plants were found to have dead primary broomrape shoots attached to their root systems under the ground. Broomrape-susceptible lines were infected with broomrape shoots that emerged above the soil. The susceptible plants showed different degrees of broomrape attack intensity.

Example 2

Molecular Mapping of the QTL Conferring Broomrape System 2 Resistance

One approach to determining which alleles play a part in a phenotypic trait is to compare plant strains with highly divergent phenotypes for the trait of interest. The allele distributions for an entire database of markers are analyzed for the two phenotypic groups. For example, an "Intergroup Allele Distribution" test can be conducted using GeneFlow™ version 7.0 software (GENEFLOW, Inc., Alexandria, Va.). An intergroup allele frequency analysis provides a method for finding non-random distributions of alleles between two phenotypic groups. During processing, a contingency table of allele frequencies is constructed and from this a G-statistic and probability are calculated (the G statistic is adjusted by using the William's correction). The probability value is adjusted to take into account the fact that multiple tests are being done (thus, there is some expected rate of false positives). The adjusted probability is proportional to the probability that the observed allele distribution differences between the two classes would occur by chance alone. The lower the probability value, the more significant is the association between the marker genotype at that locus and the phenotype of interest, in this case the *Orobanche* resistance phenotype. A more complete discussion of the derivation of the probability values can be found in the GeneFlow™ version 7.0 software documentation. See also, Sokal and Rolf (1981), *Biometry: The Principles and Practices of Statistics in Biological Research,* 2nd ed., San Francisco, W. H. Freeman and Co. In this analysis, adjusted probabilities less than 0.05 are considered significant (the marker and the phenotype show linkage disequilibrium), and adjusted probabilities less than approximately 0.01 are considered highly significant. Allele classes represented by less than a minimum number of observations across both groups are not included in the statistical analysis.

The underlying logic is that markers with significantly different allele distributions between the resistant and susceptible groups might be associated with the trait and can be used to differentiate them. The present analysis examined one marker locus at a time and determined if the allele distribution within the tolerant group was significantly different from the allele distribution within the susceptible group. A statistically different allele distribution is an indication that the marker is linked to a locus that is associated with *Orobanche* resistance.

To identify sunflower genetic marker loci associated with resistance to *Orobanche*, a mapping population of 182 F2:3 sunflower lines was derived from the cross of U0151 LG (resistant parent) X E0005LG (susceptible parent). Resistance or susceptibility of the parent lines had previously been determined. Genomic DNA was isolated from the parent and progeny plants and analyzed in PCR reactions using publicly-available amplification primers specific for a large number of SSR markers that collectively covered all chromosomes in the sunflower genome. Progeny and parent plants were also scored in the field for *Orobanche* resistance. As a result of this analysis, a putative locus for broomrape race H system 2 resistance was mapped to linkage group 4 (LG-04) of the public sunflower consensus map, approximately 3 cM from SSR HT0664-CA (Wills, D. M. and Burke, J. M. (2007) *Genetics* 176:2589-2599). See FIG. 1.

To saturate the region with more markers from the sunflower reference linkage map (Yu, J., et al., (2003) *Crop Science* 43:367-387; Gentzbittel, L., et al., (1999) *Theor Appl Gen* 99:218-234), two SNP markers were identified as potential markers of interest, HT0183 and HT090 (Lai, et al., (2005) *Theor. Appl. Gen.* 11:1532-1544; Pérez-Vich, B. (2004) *Theor. Appl Gen.* 109:92-102). See FIG. 2. Primers (SEQ ID NOS: 5 and 6) were designed which could serve to amplify a fragment of approximately 278 bp, and PCR was run on the two parental lines, U0151 LG and E0005LG, as well as U01P6LM and a fourth line. A PCR product was amplified in each of the four lines using the HT183-F1/HT183-R1 primer pair. The resulting sequences of these four bands indicated that there are three potentially true SNP marker loci. These three SNPs are marked with asterisks in the alignment provided as FIG. 3.

A TAQMAN® assay (Roche Molecular Systems, Inc.) was then designed and implemented for detection of the HT183 SNP using the primers of SEQ ID NOS: 3 and 4. Association of the HT183 SNP with BRSII resistance was validated using samples of breeding lines with known disease-resistance phenotypes. The genotyping result was consistent with the observed field result in 98.2% of samples (N=167). The HT183 SNP locus was mapped to a location 1 cM away from the previously-identified QTL locus for *Orobanche* resistance on Linkage Group 4.

The 167 progeny were selected from the five populations listed in FIG. 4.

The invention claimed is:

1. A method of identifying a sunflower plant or sunflower germplasm having a phenotype of System II resistance to *Orobanche*, comprising detecting in a sunflower plant or sunflower germplasm at least one single-nucleotide polymorphism of a marker locus that is associated with said phenotype, wherein the marker locus is represented by SEQ ID NO: 2 or displays a recombination frequency of less than 10% with respect to the marker locus of SEQ ID NO: 2 and maps to Linkage Group 4.

2. The method of claim 1, wherein the detecting comprises amplifying the marker locus or a portion of the marker locus and detecting the resulting amplified marker amplicon.

3. The method of claim 2, wherein the amplifying comprises:
   a) admixing an amplification primer or amplification primer pair with a nucleic acid isolated from the sunflower plant or germplasm, wherein the primer or primer pair is complementary or partially complementary to at least a portion of the marker locus, and is capable of initiating DNA polymerization by a DNA polymerase using the sunflower nucleic acid as a template; and
   b) extending the primer or primer pair in a DNA polymerization reaction comprising a DNA polymerase and a template nucleic acid to generate at least one amplicon.

4. The method of claim 3, wherein the primer or primer pair is selected from the group consisting of SEQ ID NO: 3, 4, 5, 6, 7, 8, 9, and 10.

5. A method of breeding comprising crossing the sunflower plant or germplasm identified by the method of claim 1 with a second sunflower plant or germplasm.

6. The method of claim 5, further comprising one or more steps of backcrossing, selfing, outcrossing, and selection of plants.

7. The method of claim 6 further comprising the step of molecular marker analysis of DNA samples isolated from one or more plants resulting from use of the method, wherein said analysis identifies a plant comprising at least one polymorphism of SEQ ID NO: 2 associated with Orobanche resistance.

8. The method of claim 7, wherein said identified plant displays an increased resistance to *Orobanche* when compared to the second sunflower plant or germplasm.

9. The method of claim 7, further comprising evaluating said identified plant for System I resistance to *Orobanche*.

10. The method of claim 7, further comprising introducing at least one gene by introgression or transformation.

11. The method of claim 10, wherein said introduced gene confers insect resistance, herbicide tolerance, disease resistance, or abiotic stress tolerance.

* * * * *